US005763686A

United States Patent [19]

McCloskey et al.

[11] Patent Number: 5,763,686
[45] Date of Patent: *Jun. 9, 1998

[54] METHOD FOR PREPARING 1,1,1-TRIS(4-HYDROXYPHENYL)ETHANE

[75] Inventors: Patrick Joseph McCloskey, Watervliet; Eric James Pressman, East Greenbush, both of N.Y.

[73] Assignee: General Electric Company, Schenectady, N.Y.

[*] Notice: The portion of the term of this patent subsequent to Dec. 4, 2016, has been disclaimed.

[21] Appl. No.: 766,092

[22] Filed: Dec. 16, 1996

[51] Int. Cl.$^6$ .................................................. C07C 39/12
[52] U.S. Cl. .................................................. 568/720
[58] Field of Search ................................ 568/720, 725

[56] References Cited

U.S. PATENT DOCUMENTS

| | | |
|---|---|---|
| 3,579,542 | 5/1971 | Meyer . |
| 4,992,598 | 2/1991 | Strutz . |
| 5,130,467 | 7/1992 | Mott . |
| 5,463,140 | 10/1995 | Wehmeyer et al. . |

*Primary Examiner*—Gary Geist
*Assistant Examiner*—Karl J. Puttlitz, Jr.
*Attorney, Agent, or Firm*—William H. Pittman

[57] ABSTRACT

1,1,1-Tris(4-hydroxyphenyl)ethane, a branching agent for polycarbonates, is prepared by the reaction of phenol with 2,4-pentanedione in the presence of sulfuric acid and at least one mercapto sulfonic acid such as 3-mercaptopropanesulfonic acid as promoter. By employing specific proportions of the promoter and sulfuric acid, high product yields can be obtained in relatively short times.

12 Claims, No Drawings

METHOD FOR PREPARING 1,1,1-TRIS(4-HYDROXYPHENYL)ETHANE

BACKGROUND OF THE INVENTION

This invention relates to the preparation of branching agents for polycarbonates, and more particularly of 1,1,1-tris(4-hydroxyphenyl)ethane, hereinafter sometimes "THPE".

THPE, disclosed in U.S. Patent Nos. 3,579,542 and 4,992,598, is in common use as a branching agent for polycarbonates. As such, it may be incorporated in reaction mixtures also containing dihydroxyaromatic compounds such as bisphenol A and carbonate sources such as phosgene or diphenyl carbonate.

THPE is commonly prepared by the reaction of 4-hydroxyacetophenone with phenol, said reaction being analogous to the reaction of phenol with acetone to form 2,2-bis(4-hydroxyphenyl)propane (hereinafter "bisphenol A"). This method is, however, economically undesirable because of the high price of 4-hydroxyacetophenone.

Copending, commonly owned application Ser. Nos. 08/583,264 and [RD-25346] disclose a method of preparing THPE by the reaction of an excess of phenol with 2,4-pentanedione under acidic conditions and in the presence of an effective amount of a mercapto compound such as 3-mercaptopropionic acid as promoter. 2,2-Bis(4-hydroxyphenyl)propane ("bisphenol A") is a major by-product, but the reactions leading to THPE and bisphenol A appear to occur independently of each other for the most part.

This method, disclosed in said applications as affording THPE in yields on the order of 60%, has promise as an alternative commercial route. However, it is usually found that very long reaction times are required to afford THPE in high yield at temperatures on the order of 40° C. At higher temperatures, particularly 60° C. and higher, reaction times can be shortened but optimum yields may nevertheless not be attained owing to the occurrence of competing reactions such as decomposition and/or self-condensation of 2,4-pentanedione.

The overall result, for the most part, is that THPE yields of 55% of theoretical or higher are attainable only by the use of reaction times of at least 40 hours. Such lengthy procedures are undesirable for commercial use.

U.S. Pat. No. 5,463,140 discloses the use of mercapto sulfonic acids as promoters for the condensation of phenols with carbonyl compounds to produce polyphenols. One of the carbonyl compounds disclosed is acetylacetone (2,4-pentanedione), but the identity of any product obtained therefrom is not disclosed. The only mention found in this patent of the use of an inorganic acid in this reaction is in Example 2, wherein phenol is condensed with 9-fluorenone in the presence of 3-mercaptopropanesulfonic acid produced by neutralization of the sodium salt with a slight excess of sulfuric acid.

It would be highly desirable, therefore, to develop variants of the previously disclosed method for preparing THPE from phenol and 2,4-pentanedione which would afford the product in yields of at least 55% of theoretical with reaction times of 24 hours or less, and at temperatures which minimize side reactions which consume the essential reactant 2,4-pentanedione.

SUMMARY OF THE INVENTION

The present invention provides a method for producing THPE from phenol and 2,4-pentanedione in particularly high yield under relatively mild conditions, and at reaction times of 24 hours or even less.

The invention is a method for preparing 1,1,1-tris(4-hydroxyphenyl)ethane which comprises contacting, at a temperature in the range of about 30°–55° C., a mixture of phenol and 2,4-pentanedione with at least 0.8% by weight, based on phenol, of at least one mercapto sulfonic acid as promoter and sulfuric acid in a ratio of equivalents to said mercapto sulfonic acid of at least about 7.5:1, the molar ratio of phenol to 2,4-pentanedione being at least about 6:1, to produce a mixture of bisphenol A and said 1,1,1-tris(4-hydroxyphenyl)ethane.

DETAILED DESCRIPTION; PREFERRED EMBODIMENTS

According to the present invention, phenol and 2,4-pentanedione are employed in a molar ration of at least about 6:1 and preferably about 6–9:1. The reagents may be blended in any order; it is frequently advantageous to introduce the 2,4-pentanedione last and incrementally (e.g., dropwise) in order to maintain the phenol in large excess at all times. While a solvent may be employed, it is usually neither necessary nor preferred.

Further essential constituents are at least one mercapto sulfonic acid and sulfuric acid. The mercapto sulfonic acid may be any of those disclosed in the aforementioned U.S. Pat. No. 5,463,140, the disclosure of which is incorporated by reference herein. It is preferably a monomeric mercapto sulfonic acid and more preferably a mercaptoalkanesulfonic acid. The alkylene groups in the more preferred compounds most often contain about 1–15 and preferably about 1–5 carbon atoms. The most preferred compound, by reason of its availability and particular effectiveness, is 3-mercaptopropanesulfonic acid. It may be introduced as the free acid or as a salt thereof, typically an alkali metal salt such as the sodium salt; upon contact with the sulfuric acid, said salt is converted to the free sulfonic acid.

Typically, the sulfuric acid is introduced as the commercially available 97% material. It has been found that the combination of sulfuric acid and a mercapto sulfonic acid is particularly effective to afford THPE in high yield. This is shown by the fact that yields decrease when the mercapto sulfonic acid is replaced by 3-mercaptopropionic acid. They also decrease substantially when a combination of 3-mercaptopropionic acid and a simple sulfonic acid, such as methanesulfonic or p-toluenesulfonic acid, is employed.

The proportion of mercapto sulfonic acid in the reaction mixture, calculated as free acid, is at least 0.8% and most often from 0.8% to about 3.0% by weight based on phenol. Larger proportions than 3.0% do not substantially improve yield. However, at proportions smaller than 0.8% the yield decreases noticeably.

The proportion of sulfuric acid in the reaction mixture is relatively high: a ratio of equivalents to equivalents of mercapto sulfonic acid of at least about 7.5:1 and generally about 7.5–10.0:1. A further amount of 1 equivalent of sulfuric acid will be needed to neutralize any salt of said mercapto sulfonic acid which may be employed in place of the free acid.

Reaction temperatures employed according to the invention are in the range of about 30°–55° and preferably about 40°–50° C. At temperatures below 30°, the reaction may be very slow, while above 55°, competing reactions involving 2,4-pentanedione may decrease THPE yield. It is often preferred to conduct the reaction in an inert atmosphere such as nitrogen or argon. Application of a mild vacuum may also be beneficial.

The THPE produced by the method of the invention is preferably purified in a specific series of steps. The first step, which takes place upon completion of the reaction between 2,4-pentanedione and phenol as described hereinabove, is combination of the crude product, most often a mixture of THPE and bisphenol A with a small proportion of unreacted phenol, with a chlorinated alkane, most often methylene chloride. A sufficient quantity of methylene chloride is generally a volume ratio to crude product of at least about 2.5:1 and most often about 3:1. Prior or subsequent to methylene chloride addition, the crude product may be neutralized by addition of a basic reagent such as sodium hydroxide or sodium bicarbonate.

Upon preparing the combination with the chlorinated alkane, a THPE-enriched mixture of THPE and bisphenol A (hereinafter "enriched mixture") precipitates and can be isolated. This enriched mixture may contain as much as about 98% by weight THPE, with the balance being predominantly bisphenol A.

Conversion of the crude product to the enriched mixture is accompanied by a substantial decrease in color. Most often, the APHA color number of the crude product is about 2000 or greater, while that of the enriched mixture is on the order of 1000. For use as a branching agent for polycarbonates, however, an essentially colorless product having a color number of 150 or less is generally required. Since further purification and decolorization cannot be achieved by repeated washings with chlorinated alkane, further purification steps may be necessary.

In the first further purification step, the enriched mixture may be contacted with a methanol-water mixture containing at least 30% methanol by volume. It has been found that when the volume of methanol in the methanol-water mixture is less than 30%, a substantial amount of bisphenol A, typically greater than 2% by weight, remains in the product. Most often, the proportion of methanol in the methanol-water mixture is on the order of 30–40% by volume. To suppress dissolution of THPE in the methanol-water mixture, said mixture is saturated with THPE prior to use. The methanol-water mixture so saturated is hereinafter sometimes designated "wash liquid".

Contact between the wash liquid and the enriched mixture may be by slurrying or simply by washing. Typical contact temperatures are in the range of about 25°–50° C. The wash liquid may further contain a decolorizing proportion, most often about 0.01–0.10% by weight, of an alkali metal borohydride or dithionite, preferably sodium borohydride ($NaBH_4$) or sodium dithionite ($Na_2S_2O_3$). Sodium borohydride is preferred.

When contact is by slurrying, purified THPE is recovered by filtration, most often preceded by cooling to about 25° C. if a higher temperature has been employed to produce the slurry, from the THPE slurry thus obtained. The purified THPE produced in this step is generally at least 98% pure, with bisphenol A being the only impurity present in substantial amount.

The methanol-water filtrate recovered from the purified THPE is itself THPE-saturated. Therefore, it may be recycled for use as wash liquid with further enriched mixture.

The purified THPE obtained from the above-described purification method is generally of a light cream color. It may be converted to essentially pure white product by dissolution in methanol and treatment with a decolorizing proportion of alkali metal borohydride or dithionite. The initially amber solution turns pale yellow upon such treatment. It may be filtered and maintained at a temperature in the range of 25°–50° C., after which water at the same temperature may be added slowly with stirring and the solution cooled if necessary to ambient temperature, resulting in the precipitation of essentially pure THPE as a white solid.

When contact between wash liquid and the enriched mixture is by washing rather than slurrying, as by spraying the filter cake with the wash liquid, the enriched mixture thus obtained may have a somewhat higher bisphenol A content, often up to about 5% by weight. It may then be further contacted as described hereinabove with methanol containing a decolorizing proportion of alkali metal borohydride or dithionite, and, optionally, also with decolorizing charcoal. After filtration if necessary, the resulting solution may be combined with water to precipitate a final product which generally comprises at least about 96% THPE, with the balance being bisphenol A. The presence of bisphenol A in such proportions is tolerable when the product is to be used as a polycarbonate branching agent.

It is generally found that the THPE yield by the method of this invention, even after purification as described hereinabove, is at least about 55% of theoretical.

The invention is illustrated by the following examples.

EXAMPLES 1–4

To 500-ml 3-necked round bottomed flasks equipped with overhead mechanical stirrers were charged 100 g (1.06 moles) of phenol, 3 g (16.9 mmol) of sodium 3-mercaptopropanesulfonate (equivalent to 2.63 g of the free acid) and 200 mg of p-terphenyl as an internal standard. The resulting mixtures were heated to various reaction temperatures and 13.3 ml (129 mmol) of 2,4-pentandione was added in one portion. Finally, various amounts of 97% sulfuric acid were added dropwise over several minutes. After a nitrogen purge, house vacuum was applied during the course of the reaction in certain examples. Over the course of the reaction the reaction mixtures became brownish red and very thick as the product began to precipitate. The mixtures were analyzed by high pressure liquid chromatography and the reactions determined to be complete in 20 hours.

After a total permitted reaction time of 24 hours, the mixtures were diluted with 200 ml of methylene chloride. The resulting solutions were transferred to 1-l Erlenmyer flasks and diluted with methylene chloride to 450 ml total volume. The mixtures were stirred for two hours, filtered and washed.

The resulting crude products were washed with 100 ml of a water-methanol mixture (61:39 by volume) presaturated with THPE to remove additional color and minor levels of impurities. Light cream colored solids were isolated which, after drying, provided mixtures of THPE, bisphenol A and phenol. The crude yields of THPE were determined by high pressure liquid chromatography.

The results are given in Table I, in comparison with Control 1 in which an equal weight of 3-mercaptopropionic acid was substituted for the 3-mercaptopropanesulfonic acid.

TABLE I

| Example | H₂SO₄ % (wt.) | Equiv. ratio** | Temperature, °C. | THPE crude Vacuum | yield, % |
|---------|---------------|----------------|------------------|-------------------|----------|
| 1       | 5             | 8.9            | 45               | First 1.5 hrs.    | 55       |
| 2       | 6             | 10.7           | 45               | Continuous        | 59       |
| 3       | 6             | 10.7           | 50               | None              | 59       |
| 4*      | 6             | 10.7           | 50               | Continuous        | 60       |
| Control 1 | 6           | —              | 50               | None              | 51       |

*Reaction time 21 hours.
**Ratio of equivalents, H₂SO₄:sulfonic acid (in excess of amount required for neutralization of sodium salt).

The results in Table I demonstrate that crude yields of 55% or greater are regularly obtainable by the method of the invention, in contrast to Control 1 in which a similar reaction employing 3-mercaptopropionic acid as a promoter afforded a crude yield of only 51%.

EXAMPLES 5-7

The procedure of Example 4 was repeated, varying the proportion of sodium 3-mercaptopropanesulfonate. Following the described workup procedure, the crude THPE was dissolved in methanol and a small amount of borohydride was added, followed by decolorizing carbon. The mixtures were stirred for 30 minutes under nitrogen and filtered, and water containing dissolved sodium borohydride in excess of the amount needed to precipitate a purified product, was added dropwise over 1.2 hours with stirring. The solid product was filtered and dried to constant weight at 60° C., yielding a product comprising about 96.5% by weight THPE, with the balance being bisphenol A. The purified yield of THPE was calculated and the results are given in Table II, in comparison with two controls in which amounts of sulfonic acid less than 0.8% were employed.

TABLE II

| Example   | Sulfonic acid, % | THPE yield, % |
|-----------|------------------|---------------|
| 5         | 2.6              | 58            |
| 6         | 1.75             | 59            |
| 7         | 0.88             | 54            |
| Control 2 | 0.4              | 49            |
| Control 3 | 0.22             | 45            |

It is apparent that relatively high yields of product are obtained by the method of this invention, even after purification. When the proportion of sulfonic acid was less than 0.8%, however, substantially decreased yields were observed.

EXAMPLE 8

A 38-l glass-lined reactor was charged with 18.2 kg (194 moles) of phenol, 345 g of sodium 3-mercaptopropanesulfonate and 34 g of p-terphenyl as an internal standard. The mixture was heated to 50° C. under nitrogen, with stirring, and 1.03 kg of 97% sulfuric acid was added over several minutes, whereupon the mixture turned yellow and then orange. Nitrogen sparging was continued for 10 minutes after which 2.5 kg (25 moles) of 2,4-pentanedione was added over several minutes, whereupon a minor exotherm was noted. A slight vacuum was applied and stirring and nitrogen sparging were continued for 22 hours; after 20 hours, the reaction was complete as determined by high pressure liquid chromatography.

Methylene chloride, 17 l, was added slowly at 50° C. and the mixture was poured into a polyethylene drum and diluted with an additional 38 l of methylene chloride. After stirring for 2 hours at room temperature, the mixture was filtered and the filtration residue was washed with 17 l of methylene chloride, 19 l of water and 19 l of a 40:60 (by volume) methanol-water solution which had been saturated with THPE. The purified product was dried to constant weight in vacuum at 60° C., after which it was shown by analysis to consist of 94.6% THPE, 4.8% bisphenol A and 0.6% phenol by weight. The crude THPE yield was 55.8% of theoretical.

What is claimed is:

1. A method for preparing 1,1,1-tris(4-hydroxyphenyl) ethane which comprises contacting, at a temperature in the range of about 30°–55° C., a mixture of phenol and 2,4-pentanedione with at least 0.8% by weight, based on phenol, of at least one mercapto sulfonic acid as promoter and sulfuric acid in a ratio of equivalents to said mercapto sulfonic acid of at least about 7.5:1, the molar ratio of phenol to 2,4-pentanedione being at least about 6:1, to produce a mixture of bisphenol A and said 1,1,1-tris(4-hydroxyphenyl)ethane.

2. A method according to claim 1 wherein the mercapto sulfonic acid is a mercaptoalkanesulfonic acid.

3. A method according to claim 2 wherein the molar ratio of phenol to 2,4-pentanedione is about 6–9:1.

4. A method according to claim 2 wherein the proportion of mercapto sulfonic acid is from 0.8% to about 3% by weight based on phenol.

5. A method according to claim 2 wherein the mercapto sulfonic acid is introduced as an alkali metal salt which is neutralized by further sulfuric acid.

6. A method according to claim 2 wherein the mercapto sulfonic acid is 3-mercaptopropanesulfonic acid.

7. A method according to claim 2 wherein said 1,1,1-tris (4-hydroxyphenyl)ethane is purified by:

combining said mixture with a chlorinated alkane in an amount to produce a precipitate of a mixture of 1,1,1-tris(4-hydroxyphenyl)ethane and bisphenol A enriched in 1,1,1-tris(4-hydroxyphenyl)ethane, and isolating said precipitate;

contacting said precipitate with a methanol-water mixture containing at least 30% methanol by volume, said methanol-water mixture being previously saturated with 1,1,1-tris(4-hydroxyphenyl)ethane, to produce a 1,1,1-tris(4-hydroxyphenyl)ethane slurry, and recovering purified 1,1,1-tris(4-hydroxyphenyl)ethane from said slurry.

8. A method according to claim 7 wherein the chlorinated alkane is methylene chloride.

9. A method according to claim 8 wherein said methanol-water mixture further contains a decolorizing proportion of sodium borohydride.

10. A method according to claim 9 wherein said purified 1,1,1-tris(4-hydroxyphenyl)ethane is contacted with further methanol to form a solution, from which still further purified 1,1,1-tris(4-hydroxyphenyl)ethane is precipitated by combining with water.

11. A method according to claim 10 wherein said further methanol contains a decolorizing proportion of sodium borohydride.

12. A method according to claim 10 wherein said contact with further methanol also includes contact with decolorizing charcoal.

* * * * *